(12) United States Patent
Gierer et al.

(10) Patent No.: US 6,763,747 B1
(45) Date of Patent: Jul. 20, 2004

(54) SHOCK ABSORBING HAMMER AND HANDLE ASSEMBLY

(75) Inventors: Joseph T. Gierer, Glen Carbon, IL (US); David L. Pringle, Town and Country, MO (US)

(73) Assignee: Emerson Electric Co., St. Louis, MO (US)

( * ) Notice: Subject to any disclaimer, the term of this patent is extended or adjusted under 35 U.S.C. 154(b) by 0 days.

(21) Appl. No.: 09/261,643

(22) Filed: Mar. 3, 1999

Related U.S. Application Data

(63) Continuation-in-part of application No. 09/005,198, filed on Jan. 9, 1998, and application No. 09/005,199, filed on Jan. 9, 1998.
(60) Provisional application No. 60/042,057, filed on Apr. 9, 1997, and provisional application No. 60/053,305, filed on Jul. 21, 1997.

(51) Int. Cl.[7] .............................................. B25G 1/08
(52) U.S. Cl. ...................... 81/489; 16/110.1; 30/340; 81/177.1
(58) Field of Search ................................ 16/110.1, 431; 81/489, 177.1; 30/308.1, 340

(56) References Cited

U.S. PATENT DOCUMENTS

| | | |
|---|---|---|
| 1,045,145 A | 11/1912 | Hubbard |
| 1,445,514 A | 2/1923 | Johnson |
| 1,501,095 A | 7/1924 | Brock |
| 2,451,217 A | 10/1948 | Heinrich ................. 145/29 |
| 2,604,914 A | 7/1952 | Kahlen .................. 145/36 |
| 2,737,216 A | 3/1956 | Kenerson ............... 145/29 |
| 2,776,689 A | 1/1957 | Falzone ................. 145/29 |
| 2,833,323 A | 5/1958 | Strickland ............. 145/29 |
| 2,928,444 A | 3/1960 | Ivins ..................... 145/29 |
| 2,940,492 A | 6/1960 | Curry et al. ........... 145/61 |
| 3,000,414 A | 9/1961 | Corids ................... 145/29 |
| 3,704,734 A | 12/1972 | Soto et al. ............. 145/29 |
| 4,039,012 A | 8/1977 | Cook ..................... 145/29 |
| 4,183,385 A | 1/1980 | Burkybile ............. 145/29 |
| 4,216,808 A | 8/1980 | Royce .................... 145/29 |
| 4,331,193 A | 5/1982 | Tudisco ................. 145/29 |
| 4,373,565 A | 2/1983 | Soto ...................... 145/36 |
| 4,498,464 A | 2/1985 | Morgan, Jr. ........... 128/54 |
| D285,284 S | 8/1986 | Blomqvist ............. D8/77 |
| 4,639,029 A * | 1/1987 | Kolonia ............... 16/110.1 |
| 4,697,481 A | 10/1987 | Maeda ................... 81/22 |
| 4,738,166 A | 4/1988 | Yamaguchi ........... 81/22 |
| 4,831,901 A | 5/1989 | Kinne .................... 81/25 |
| 5,012,702 A | 5/1991 | Taylor ................... 81/25 |
| 5,118,117 A | 6/1992 | Denen ................. 273/420 |

(List continued on next page.)

FOREIGN PATENT DOCUMENTS

| | | | |
|---|---|---|---|
| DE | 1 273 449 | 7/1968 | |
| DE | 4206588 A1 | 1/1993 | ............ B25D/1/02 |
| FR | 1137125 | 5/1957 | |

*Primary Examiner*—James G. Smith
(74) *Attorney, Agent, or Firm*—Howrey Simon Arnold & White LLP

(57) ABSTRACT

The present invention relates to a shock absorbing hammer and handle assembly. The shock absorbing hammer includes a hammer head including a striking portion, a shaft connected to the hammer head, and a hand grip. In accordance with aspects of the present invention, a hand grip assembly suitable for use with the shock absorbing hammer includes a shell defining an outer surface and an inner cavity. An inner elastomeric layer lines the inner cavity and defines an opening adapted to receive the shaft of the item. An outer elastomeric layer surrounds the outer surface of the shell. In particular embodiments of the handle grip, the outer elastomeric layer is formed with first and second elastomeric materials, which may define different durometer hardnesses. Still further, the inner elastomeric layer may also be formed with the first elastomeric material. In accordance with another aspects of the present invention, methods of making the novel handle grip are also presented.

11 Claims, 5 Drawing Sheets

U.S. PATENT DOCUMENTS

| | | | |
|---|---|---|---|
| 5,157,807 A | * 10/1992 | Keller et al. | 16/431 |
| 5,216,939 A | 6/1993 | Swenson | 81/25 |
| 5,249,776 A | 10/1993 | Johnson | 254/26 |
| 5,259,274 A | 11/1993 | Herha | 81/20 |
| 5,289,742 A | 3/1994 | Vaughan | 81/22 |
| D347,780 S | 6/1994 | Hreha | D8/80 |
| 5,375,487 A | 12/1994 | Zimmerman | 81/22 |
| 5,408,902 A | 4/1995 | Burnett | 81/22 |
| 5,537,896 A | 7/1996 | Halder | 81/26 |
| 5,588,343 A | 12/1996 | Rust et al. | 81/489 |
| 5,601,003 A | * 2/1997 | Amtenbrink et al. | 81/489 |
| 5,713,104 A | * 2/1998 | Giampaolo, Jr. | 16/110.1 |
| 6,016,722 A | * 1/2000 | Gierer et al. | 81/22 |
| 6,128,977 A | * 10/2000 | Gierer et al. | 81/22 |
| 6,270,134 B1 | * 8/2001 | Lin | 16/431 |

* cited by examiner

SHOCK ABSORBING HAMMER AND HANDLE ASSEMBLY

CROSS-REFERENCE TO RELATED APPLICATIONS

This Application is a continuation-in-part of U.S. patent application Ser. No. 09/005,198 filed Jan. 9, 1998, which claims the benefit of U.S. Provisional Patent Application Serial No. 60/042,057 filed Apr. 9, 1997; and U.S. patent application Ser. No. 09/005,199 filed Jan. 9, 1998, which claims the benefit of U.S. Provisional Patent Application Serial No. 60/053,305 filed Jul. 21, 1997.

BACKGROUND OF THE INVENTION

1. Field of the Invention

The present invention relates to hand-held items, such as hand tools, and in particular, to devices and methods for reducing the shock and vibration caused by the use of such hand-held items.

2. Description of Related Art

Shock and vibration from the use of hand-held items, such as hand tools, are often transferred to a user's hand through the item's handle and grip. This may cause the user discomfort and increased fatigue. For instance, when a percussive tool, such as a hammer, strikes the surface of an object, part of the energy produced by the strike is used to perform desired work (e.g., drive a nail), part is converted into heat, and part is dissipated through the hammer. The energy that is dissipated through the hammer often produces undesirable results such as recoil of the hammer from the struck surface or excessive vibration of the hammer. The undesirable results produced by hammer strikes have been a persistent problem for the makers of hammers and other percussive tools.

Many users of hammers prefer the vibration-reducing feel of wood handled hammers, rather than integral steel handle/head hammers. A common perception is that the wood handle absorbs at least some of the shock of the hammer strikes rather than transferring all of the shock and vibration to the user's hand, thus reducing the user's fatigue at the end of the day as compared to using a hammer having a steel handle. However, wooden handled hammers will invariably break, typically at the wedged joint between the handle and steel head due to the prying action of nail pulling. To overcome this shortcoming, many manufacturers make integral steel handle/head hammers which hold up extremely well to nail pulling, but the shock-absorbing feature of the wood handle is lost. These problems are discussed in an article entitled "Nailing Basics," by Larry Haun in *Fine Homebuilding*, July 1997, at page 80.

In the past, various attempts have been made to reduce undesirable results produced by a hammer strike. Hammers that reduce rebound or recoil characteristics are sometimes referred to as "dead blow" hammers. One of the earliest attempts reflected in the prior art to produce a dead-blow hammer is U.S. Pat. No. 1,045,145, issued in November 1912 to E. O. Hubbard ("Hubbard"). As explained by Hubbard, when the Hubbard hammer is struck against a surface, the striking head will be forced against a cushion, such that the cushion absorbs a portion of the shock of impact produced by the strike.

Following Hubbard, several other attempts were made to reduce the undesirable results of a hammer strike and, in particular, to reduce the recoil or rebound produced when a hammer strike occurs. Several early approaches for reducing recoil in hammers are summarized in U.S. Pat. No. 2,604,914 to Kahlen ("Kahlen") issued in July 1952. In particular, Kahlen indicates that, by 1952, known methods for reducing hammer recoil included placing either a slug, a charge of round shot, or a charge of powdered material in a chamber immediately behind a striking face of the hammer, such that the object(s) placed behind the striking head will absorb some of the forces produced by the hammer strike. The particular approach disclosed in Kahlen involved the placement of a charge of irregularly-shaped, hard, heavy particles in a chamber immediately behind the striking head of a hammer.

In addition to solutions involving cushions and charge loads, several solutions utilizing resilient members, such as elastic inserts and springs, were proposed to address the hammer strike problems, whereby a portion of the energy developed from the hammer strike is dissipated through the resilient member. Other designs, such as that disclosed in U.S. Pat. No. 5,408,902, use a "lagging mass," which is positioned to move towards the striking portion of the hammer head when it impacts, thus impacting the striking portion to reduce hammer recoil.

These early approaches suffer from one or more difficulties. For example, the use of slidable weights or slugs behind the striking head of the hammer is problematic because the weights themselves develop potential energy when the hammer strikes a surface and tend to recoil, thus causing undesirable vibration or oscillation of the hammer. Further, shot-filled hammers are limited: (i) because the requirement for a hollow chamber renders the size of such hammers out of proportion to their weight; and (ii) because, unless a special shot mixture is utilized, the shot is often not useful in preventing hammer recoil. Moreover, in prior art dead blow hammers, the prying and nail pulling capability of common claw hammers has been forfeited in the attempts to reduce vibration and recoil.

Further discussion of the prior art and its associated shortcomings is provided in U.S. Pat. No. 1,045,145; U.S. Pat. No. 2,604,914; U.S. Pat. No. 2,928,444; U.S. Pat. No. 4,831,901; U.S. Pat. No. 5,118,117; U.S. Pat. No. 5,408,902; and German Patent No. 1,273,449.

The present invention addresses problems associated with the prior art.

SUMMARY OF THE INVENTION

In one aspect of the present invention, a hand grip assembly adapted to be situated about a shaft of an item includes a relatively rigid shell defining an outer surface and an inner cavity. An inner elastomeric layer lines the inner cavity and defines an opening adapted to receive the shaft of the item. An outer elastomeric layer surrounds the outer surface of the rigid shell. In particular embodiments of the handle grip, the outer elastomeric layer is formed with first and second elastomeric materials, which may define different durometer hardnesses. Still further, the inner elastomeric layer may also be formed with the first elastomeric material.

In another aspect of the present invention, a shock absorbing hammer includes a hammer head including a striking portion, a shaft connected to the hammer head, and a hand grip. The hand grip has a shell defining an outer surface and an inner cavity. An inner elastomeric layer lines the inner cavity and surrounds the shaft. An outer elastomeric layer surrounds the outer surface of the shell. The outer elastomeric layer may be formed with two elastomeric materials, which may each define different durometer hardnesses. The inner elastomeric layer may be formed with one of the elastomeric materials forming the outer elastomeric layer. Moreover, in particular embodiments, the outer elastomeric layer is adapted to fit either a user's right or left hand, for right or left handed use.

In yet another aspect of the present invention, a method of making a handle grip for an article is presented. The method includes inserting a core member into a handle shell to form an inner cavity between the core member and an inner surface of the handle shell, and situating a mold about the handle shell such that the mold seats against at least one shut-off member extending from the handle shell, so as to form at least one grip cavity and at least one handle cavity between the first mold and an outer surface of the handle shell. A liquefied first elastomeric material is injected into the inner cavity and through an opening between the inner cavity and the grip cavity, such that the first elastomeric material fills the inner cavity and the grip cavity. A liquefied second elastomeric material is injected into the handle cavity.

An alternative method of making a handle grip for an article is presented in accordance with still further aspects of the present invention. The method includes inserting a core member into a handle shell to form an inner cavity between the core member and an inner surface of the handle shell, and situating a first mold about the handle shell such that the mold seats against at least one shut-off member extending from the handle shell, so as to form at least one grip cavity between the first mold and an outer surface of the handle shell. A liquefied first elastomeric material is injected into the inner cavity and through an opening between the inner cavity and the grip cavity, such that the first elastomeric material fills the inner cavity and the grip cavity. The first mold is removed from the handle shell, and a second mold is situated about the handle shell such that the mold seats against the shut-off member so as to form at least one handle cavity between the second mold and the outer surface of the handle shell. A liquefied second elastomeric material is then injected into the one handle cavity.

BRIEF DESCRIPTION OF THE DRAWINGS

Other objects and advantages of the invention will become apparent upon reading the following detailed description and upon reference to the drawings in which.

Figure 2:
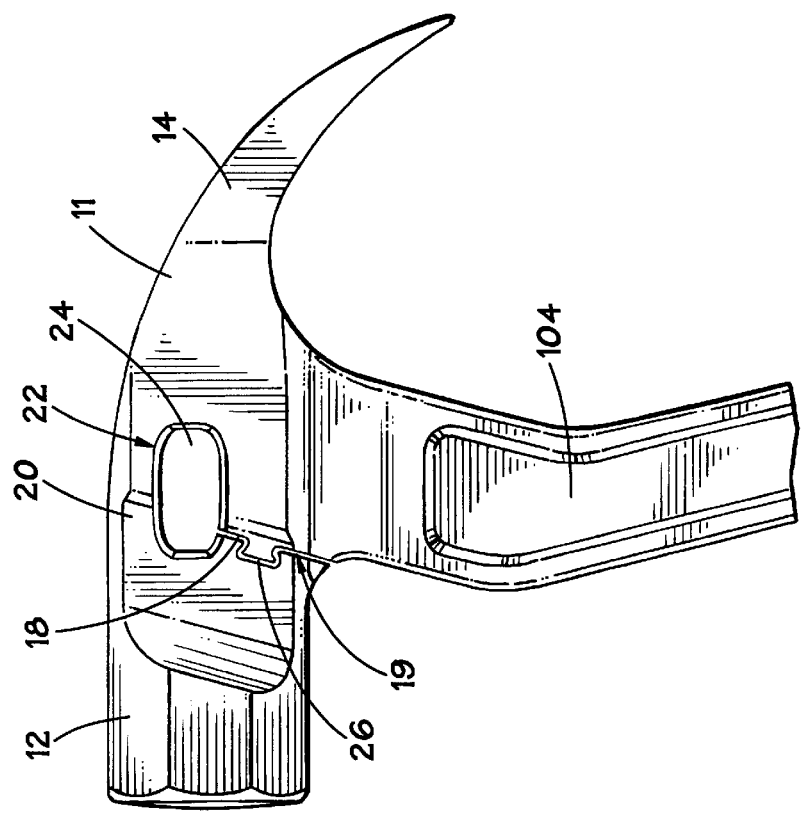
FIG. 2 is a side view of a hammer head and shaft in accordance with aspects of the present invention.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the intention is to cover all modifications, equivalents, and alternatives falling within the spirit and scope of the invention as defined by the appended claims.

DETAILED DESCRIPTION OF THE INVENTION

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure.

Figure 1:
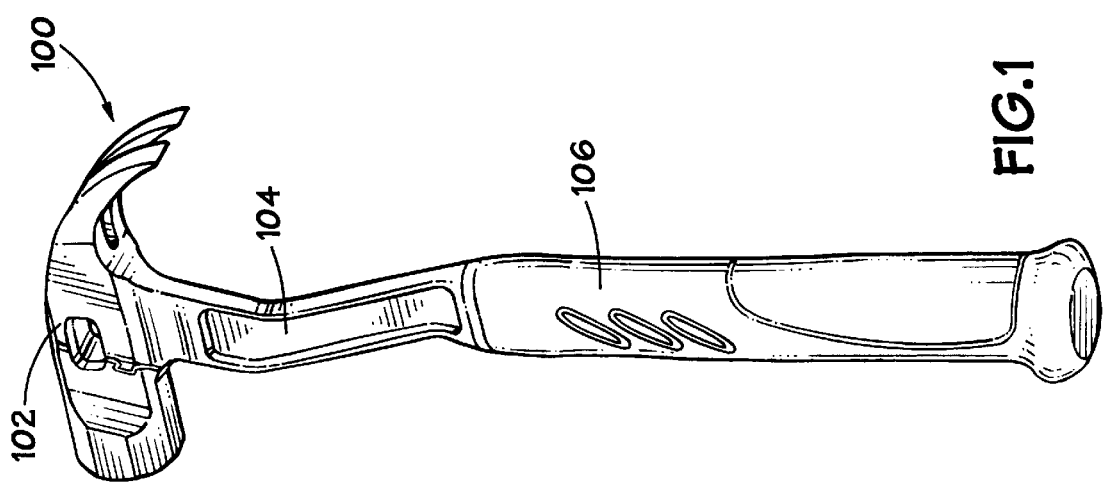
FIG. 1 is a rear perspective view of a hammer and handle assembly in accordance with an embodiment of the present invention.

Turning to the drawings, and in particular to FIG. 1, a hand tool in accordance with an embodiment of the present invention is illustrated. In general, the illustrative hand tool comprises a hammer 100 that includes a head 102, a shaft 104 and a handle grip 106. The hammer head 102 and the handle grip 106 are both adapted to reduce the shock and vibration resulting from striking an object with the hammer 100.

FIG. 2 is a side view of the hammer head 102. The hammer head 102 is generally of one-piece construction and includes a striking portion 12 and a claw portion 14. The claw portion 14 defines a generally V-shaped notch (not shown in FIG. 2) for grabbing nails during nail pulling. The shaft 104 is coupled to the head 102, and may be integrally formed therewith. The hammer head 102 defines an opening 22 formed therein, which may be filled with an elastic plug 24, which may comprise a relatively low durometer rubber plug. In the embodiment illustrated, the opening 22 extends through the head 102 generally transversely to an axis defined by the head 102.

A slit 18 is cut in the head 102 such that roughly equal mass is in the striking portion 12 and the claw portion 14. The slit 18 is about 0.010 inch to 0.040 inch, and it may be manufactured using laser cutting, wire EDM cutting or abrasive water jet cutting. The slit 18 extends from a bottom surface of the striking portion 12 which is adjacent the region where the shaft 104 connects to the head 102, to the opening 22 so that the striking portion 12 and the claw portion 14 make contact across the slit 18 in a contact area 19 to deliver the favorable lagging mass effect.

A connecting region 20 is located in the head 102 opposite the slit 18, which connects the striking portion 12 and the claw portion 14 of the head 102. In addition to connecting the striking portion 12 and the claw portion 14, the connecting region 20 acts as a flat cantilever spring, allowing the two portions of the head to contact each other in the contact area 19 upon a hammer strike. This greatly reduces hammer recoil and vibration to the hand, in turn, reducing fatigue.

The hole 22 extending through the head 102 has several purposes: (i) it accurately defines the amount of material in the connecting region 20, thus allowing for fine control over the stiffness of the flat cantilever spring by varying the size of the hole 22; (ii) its radii serve as stress relievers; and (iii) the elastic plug 24 which fills the hole 22 further defines the stiffness of the flat cantilever spring and minimizes tuning fork-like vibrations that may otherwise occur upon a hammer strike.

The slit 18 runs from the hole 22 to the bottom of the hammer head 102, which allows the slit 18 to close up when the claw portion 14 is used for nail pulling, thus preventing high tensile stresses from developing in the connecting region 20. In the embodiment illustrated in FIG. 2, the slit 18 is formed such that the striking portion 12 and the claw portion 14 of the hammer head 102 form interlocking "puzzle" pieces 26 ensuring that the slit 18 will not completely open under any circumstance. In the particular embodiment illustrated, the slit 18 defines a generally dovetail shape, which simplifies the process of cutting the slit 18 during manufacture of the hammer 100.

Figure 3:
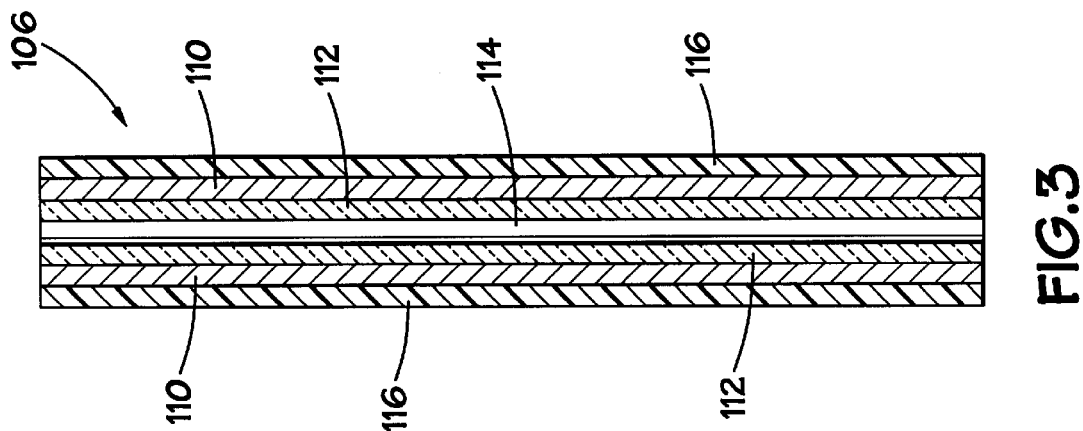
FIG. 3 is a sectional view schematically illustrating aspects of a handle grip in accordance with the present invention.

Referring now to FIG. 3, aspects of a handle grip 106 in accordance with the present invention are conceptually illustrated. The handle grip 106 includes a handle shell 110, which may be relatively rigid. The shell 110 defines an inner cavity that is lined with an inner elastomeric layer 112. The inner elastomeric layer 110 defines an opening 114 that is adapted to receive a shaft or handle of an item, such as the shaft 104 of the hammer 100. An outer surface of the shell 110 is surrounded by an outer elastomeric layer 116 that is to be gripped by a user. The shell 110 functions to support the handle grip assembly 106 and isolate the shaft or handle received within the opening 114 of the inner elastomeric layer 112 from a user's hand. The inner elastomeric layer 112 absorbs at least some of the shock and vibration transferred to a shaft or handle received in the opening 114 from use of the item to which the handle grip 106 is attached.

Figure 4:
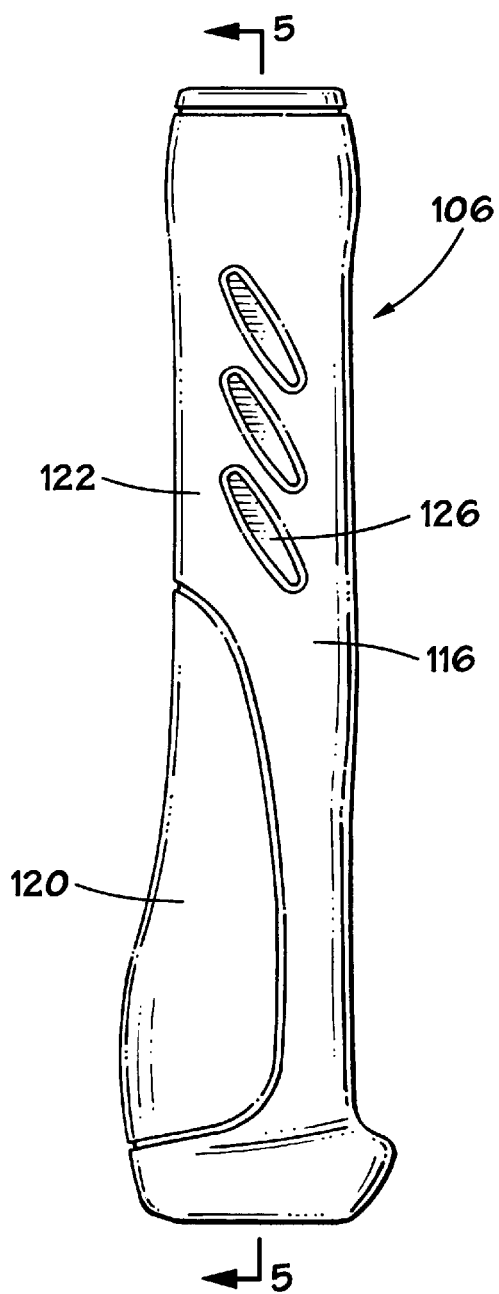
FIG. 4 is a side view of an exemplary handle assembly in accordance with an embodiment of the present invention.
Figure 5:
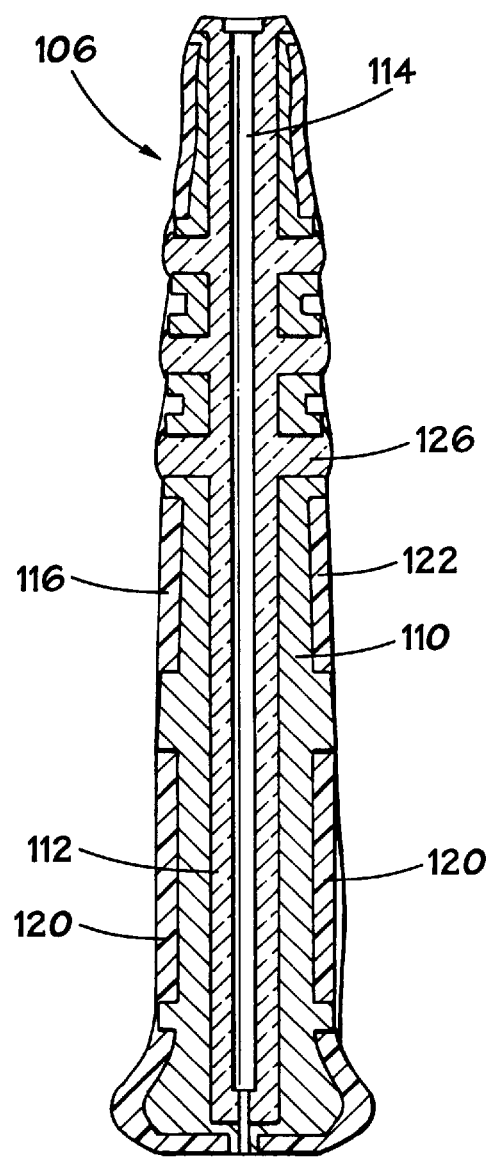
FIG. 5 is a sectional view of the handle assembly illustrated in FIG. 4, taken along line 5—5 of FIG. 4.

FIG. 4 and FIG. 5 illustrate a particular embodiment of the handle grip 106. FIG. 4 shows a side view of the handle grip 106. As mentioned above, the handle grip 106 is adapted to reduce the shock and vibration transferred to a user's hand from the object to which the handle grip 106 is attached. In particular embodiments, such as the embodiment illustrated in FIG. 1, the handle grip 106 is adapted to receive the shaft 104 of a hammer 100. The novel handle grip 106, however, may be configured for use with other items, especially other hand tools such as hammers, hatchets, etc. For example, the handle grip 106 may be adapted for use with the various dead-blow and shock-absorbing hammers disclosed in copending U.S. patent application Ser. Nos. 09/005,198 and 09/005,199, which are both incorporated by reference in their entirety. Adapting the handle grip 106 for use with other hammer configurations, other hand tools, or other hand-held items in which it is desirable to reduce shock and vibration would be a routine undertaking for one skilled in the art having the benefit of this disclosure.

The sectional view of FIG. 5 shows the shell 110, the inner elastomeric layer 112 with the opening 114 therein for receiving a shaft of an object such as the hammer shaft 104, and the outer elastomeric layer 116. The inner and outer elastomeric layers 112, 116 may be suitably formed out of viscoelastic material or a thermoplastic rubber (TPR) material such as SANTOPRENE, which is available from Advanced Elastomer Systems. Further, the outer elastomeric layer 116 may be formed of two different elastomeric materials to provide an improved holding surface for a user. For example, in the embodiment illustrated in FIG. 4 and FIG. 5, the outer elastomeric layer 116 includes a primary gripping portion 120 that is adapted to generally fit in a user's palm (referred to as the "grip portion"), which is comprised of a first elastomeric material having a given durometer hardness. The outer elastomeric layer 116 further includes a "handle" portion 122 that is comprised of a second elastomeric material having durometer hardness different than the given hardness.

Figure 6:
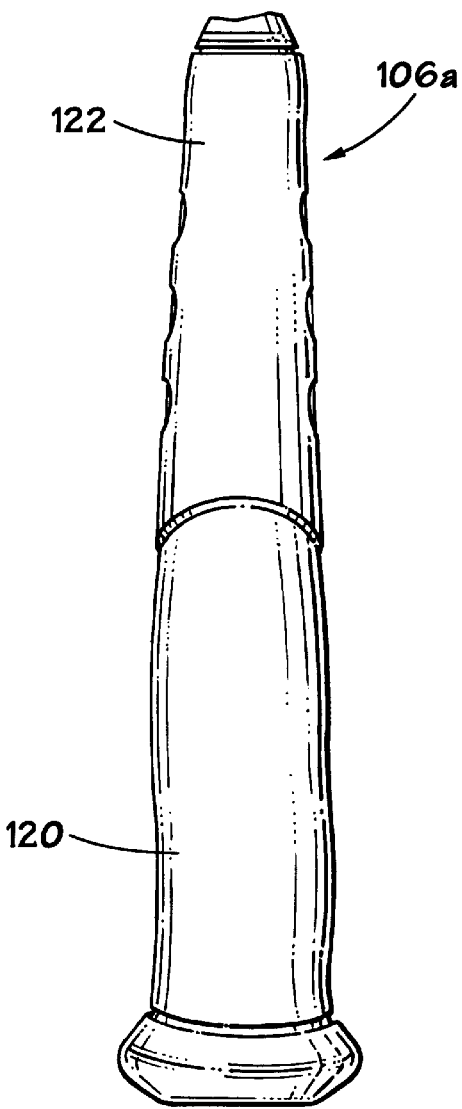
FIG. 6 is an elevation view of a right-handed version of a handle grip in accordance with the present invention.

In a particular embodiment, the first elastomeric material used in the grip portion 120 defines a durometer hardness softer than that of the second elastomeric material, which forms the handle portion 122. For example, the first and second elastomeric materials may define durometer hardnesses of 45 and 60, respectively. Thus, a softer material is used for the primary grip portion 120 that is in contact with the user's palm, so as to absorb more shock and vibrations from use of the object to which the handle grip 106 is attached. Still further, as shown in FIG. 6, the inner elastomeric layer 112 may also be comprised of the first elastomeric material, placing the softer elastomeric material against the shaft to better absorb shock and vibration. The remaining handle portion 122 uses the higher durometer material for better wear-and-tear since it is generally a non-gripping portion.

Figure 7:
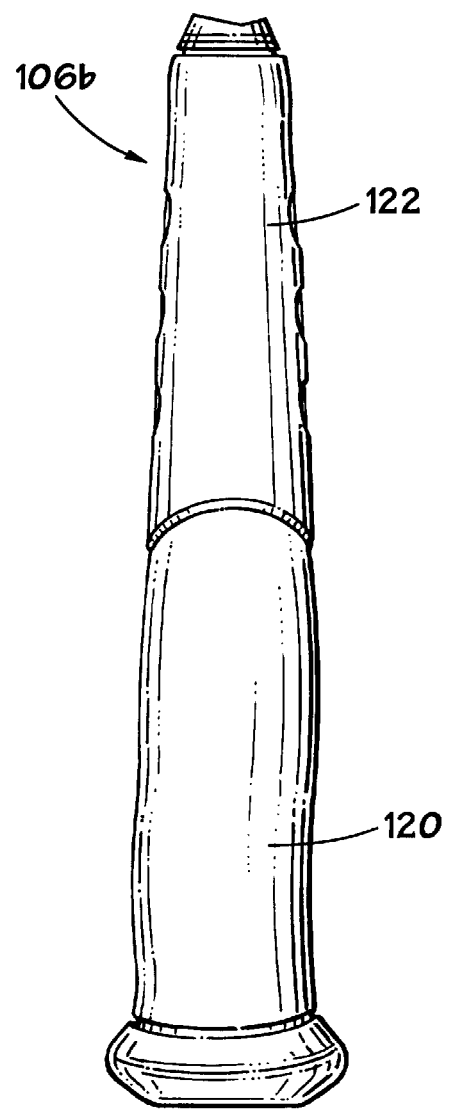
FIG. 7 is an elevation view of a left-handed version of a handle grip in accordance with the present invention.

To provide even further comfort to a user, the handle grip 106 may be specifically adapted to be held by a user's right or left hand. Right-handed 106a and left-handed 106b embodiments are illustrated in FIG. 6 and FIG. 7, respectively. Among other things, as shown in the right-handed embodiment 106a of FIG. 6, the grip portion 120 extends to the right side (as viewed in FIG. 6) and around the handle grip 106 to provide maximum contact with the user's palm. The grip portion 120 adapted to fit a user's palm in the left-handed embodiment 106b (shown in FIG. 7) is generally a mirror image of the right-handed version 106a.

Figure 8:
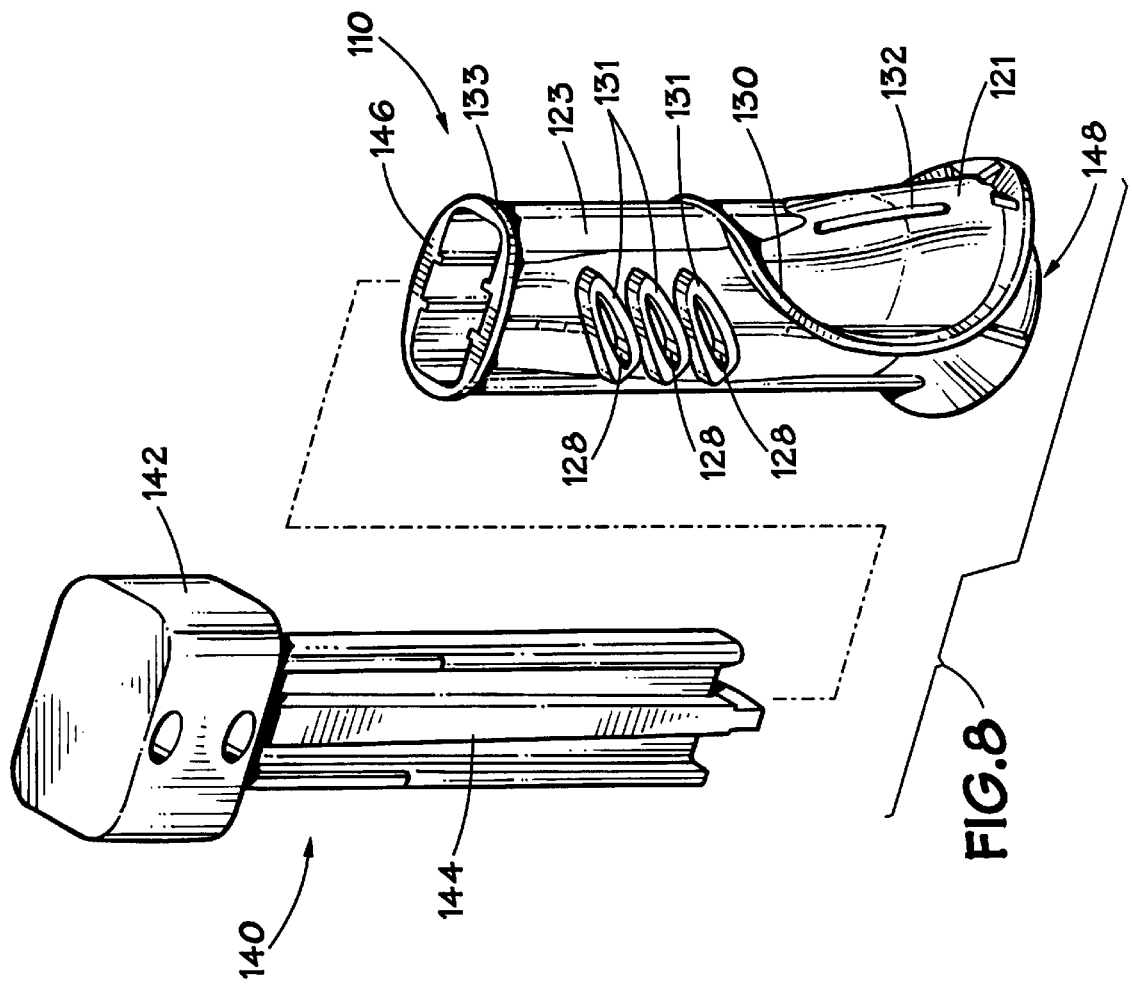
FIG. 8 is a perspective view of a shell and core member suitable for use in the exemplary handle assembly illustrated in FIGS. 4 and 5.

Referring now to FIG. 8, an embodiment of a shell 110 suitable for use in the embodiment of the handle grip 106 shown in FIG. 4 is illustrated. The shell 110 may be formed out of polypropylene, for example, via an injection molding process. The shell 110 defines one or more shut-off members 130, 131, 133 extending therefrom. The specific embodiment illustrated includes a shut-off member 130 defining the grip portion 120 that is adapted to fit in a user's palm. The shut-off member 130 functions as a boundary between the grip portion 120 and the handle portion 122, which comprise the first and second elastomeric materials, respectively. Additional shut-off members 131 may be provided, such as those on either side of the handle grip 106 in FIG. 8, which define additional areas 126 of the outer elastomeric layer 116 that are formed with the first elastomeric material.

Figure 9:
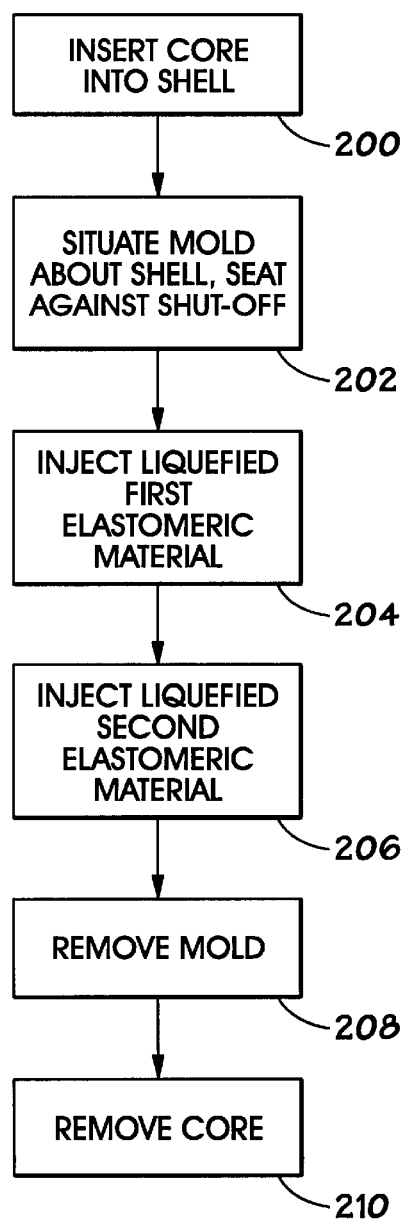
FIG. 9 is a flow diagram illustrating a process for making a handle grip in accordance with the present invention.

In accordance with other aspects of the present invention, FIG. 9 illustrates a novel method for making a handle grip. Referring to FIG. 8, the shell 110 defines an opening adapted to receive a core member 140. In block 200 of FIG. 9, the core member 140 is inserted into the shell 110 so as to form an inner cavity between the core member 140 and the inner surface of the shell 110. The inner cavity defines the area that will become the inner elastomeric layer 112. In the embodiment shown in FIG. 8, the core member 140 includes an upper portion 142 and a lower portion defining a protruded member 144 that slides into the shell 110.

In block 202, a mold defining the shape of the outer elastomeric layer 116 is situated about the shell 110, such that the mold seats against the shut-off members 130, 133. This forms at least one outer cavity. In the embodiment illustrated in FIG. 8, the outer cavities comprise a grip cavity 121 in the area that will become the grip portion 120 when filled with the first elastomeric material, and a handle cavity 123 in the area that will become the handle portion 122 when filled with the second elastomeric material.

The first elastomeric material, in a liquefied state, is injected into the inner cavity, in block 204. The shell 110, as illustrated in FIG. 8, defines an opening 132 extending from the inner cavity to the grip cavity 121 defined by the shut-off member 130. Thus, the liquefied first elastomeric material flows into the inner cavity and through the opening 132, and into the grip cavity 121 to form the grip portion 120 of the handle grip 106. In the particular embodiment illustrated, the areas of the shell 110 defined by the additional shut off members 131 each include at least one opening 128 through the shell 110, such that the liquefied first elastomeric material flows from the inner cavity and through the openings 128 to form the additional areas 126 of the outer elastomeric layer 116 comprising the first elastomeric material.

In block 206, the second elastomeric material, in a liquefied state, is injected into the handle cavity 123 to form the handle portion 122. The mold and the inner core 140 may then be removed (blocks 208, 210), leaving the opening 114 in the inner elastomeric layer 112 for receiving the object to which the handle grip 106 is to be attached. The provision of the shut-off member 130 allows forming the outer elastomeric layer 116 using elastomeric materials having different hardnesses and/or colors. The core member 140 prevents the second elastomeric material from flowing into the inner cavity.

Figure 10:
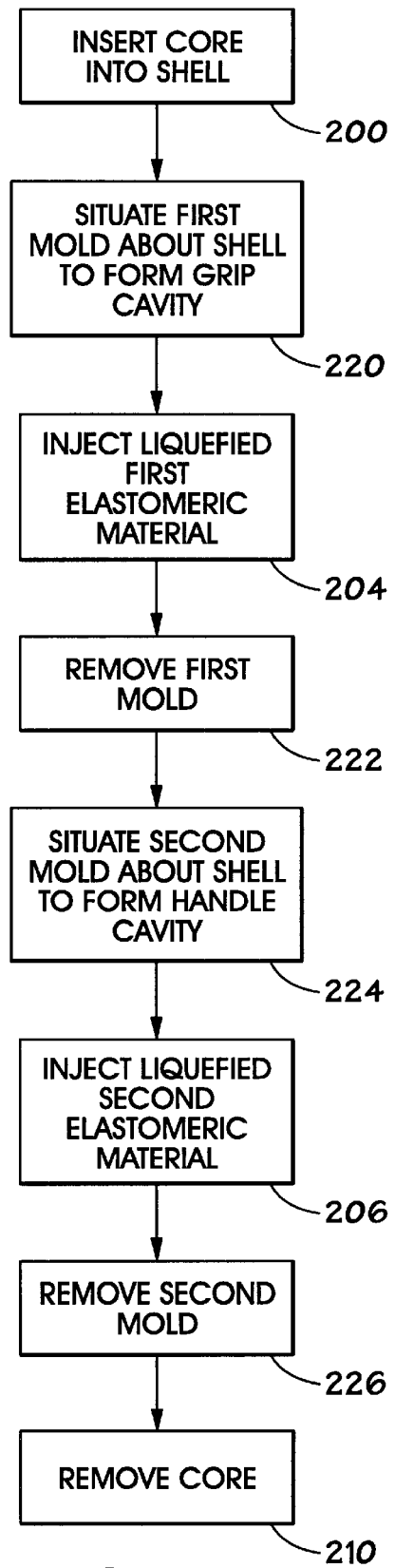
FIG. 10 is a flow diagram illustrating an alternative process for making a handle grip in accordance with the present invention.

In an alternative method in accordance with the present invention, two separate molds are used to form the grip portion 120 and the handle portion 122 of the outer elastomeric layer 116. FIG. 10 is a flow diagram illustrating this alternative method. As in the method illustrated in FIG. 9, in block 200 of FIG. 10, the core member 140 is inserted into the shell 110 to form the inner cavity between the core member 140 and the inner surface of the shell 110. In block 220, a first mold defining the shape of the grip portion 120 of the outer elastomeric layer 116 is situated about the shell 110. The first mold includes a section that defines the grip cavity 121 between the mold and the outer surface of the shell 110, and the remainder of the first mold is placed directly against the shell 110, such that the remainder of the first mold abuts the shut-off member 130.

The first elastomeric material, in a liquefied state, is injected into the inner cavity, in block 204, such that it flows into the inner cavity and through the opening 132, and into the grip cavity 121. Since the remaining portion of the first mold is placed directly against the outer surface of the shell 110, it insures that the first elastomeric material does not flow into the area that will become the handle portion 122 of the outer elastomeric layer 116. In block 222, the first mold is removed from the shell 110, and a second mold is situated about the shell 110 in block 224. The second mold forms the handle cavity 123, and is adapted so as to seat against the shut-off member 130 and against the grip portion 120 formed with the first elastomeric material.

In block 206, the second elastomeric material, in a liquefied state, is injected into the handle cavity 123 to form the handle portion 122. The second mold, which is seated against the shut-off members 130, 133 and the grip portion 120, prevents the second elastomeric material from mixing with the first elastomeric material forming the grip portion 120. The second mold and the core member 140 may then be removed in block 226 and block 210.

In specific implementations of the processes illustrated in FIG. 9 and FIG. 10, the upper portion 142 of the core member 140 forms the top of the inner elastomeric layer 112. The mold seals against the shut-off member 133 to prevent the liquefied first elastomeric material from flowing from the inner cavity into the handle cavity 123. With the embodiment of the shell 110 illustrated in FIG. 8, the first elastomeric material is injected into the shell through at least one opening (not shown) in a bottom portion 148 of the shell 110. Moreover, the protruded member 144 of the core member 140 fits tightly within the shell 110 to support the inside of the shell 110, preventing it from collapsing when the mold is situated thereabout and the second elastomeric material is injected over the shell 110 into the handle cavity 123.

The particular embodiments disclosed above are illustrative only, as the invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular embodiments disclosed above may be altered or modified and all such variations are considered within the scope and spirit of the invention. Accordingly, the protection sought herein is as set forth in the claims below.

What is claimed is:

1. A hand grip assembly adapted to be situated about a shaft of an item, comprising:

a rigid shell defining an outer surface and an inner surface;

an inner elastomeric layer substantially lining the entire inner surface and defining an opening adapted to receive the shaft; and an outer elastomeric layer surrounding the outer surface of the rigid shell.

2. The hand grip assembly of claim 1, wherein the outer elastomeric layer comprises first and second elastomeric materials.

3. A hand grip assembly adapted to be situated about a shaft of an item, comprising:

a rigid shell defining an outer surface and an inner cavity;

an inner elastomeric layer lining the inner cavity and defining an opening adapted to receive the shaft; and an outer elastomeric layer surrounding the outer surface of the rigid shell, the outer elastomeric layer comprising first and second elastomeric materials.

4. The hand grip assembly of claim 1, wherein the inner and outer elastomeric layers each comprise a thermoplastic rubber material.

5. The hand grip assembly of claim 1, wherein the inner elastomeric layer substantially lines the entire inner cavity.

6. The hand grip assembly of claim 1, wherein the first elastomeric material of the outer elastomeric layer is positioned to generally fit in the palm of a user gripping the hand grip assembly.

7. The hand grip assembly of claim 1, wherein the first and second elastomeric materials each define a different hardness.

8. The hand grip assembly of claim 5, wherein the first elastomeric material defines a hardness softer than the second elastomeric material.

9. The hand grip assembly of claim 1, wherein the inner elastomeric layer comprises the first elastomeric material.

10. The hand grip assembly of claim 1, wherein the outer elastomeric layer is adapted to fit one of a right or a left hand.

11. The hand grip assembly of claim 1, wherein the outer surface of the rigid shell defines at least one shut-off member extending therefrom, the shut-off adapted to form a boundary between the first and second elastomeric materials of the outer elastomeric layer.

* * * * *